US012776417B2

(12) United States Patent
Gaffney

(10) Patent No.: US 12,776,417 B2
(45) Date of Patent: Oct. 27, 2026

(54) METHODS AND APPARATUS FOR AUTOMATED EXTRACTION OF CORONARY ARTERY DISEASE INFORMATION FROM UNSTRUCTURED MEDICAL DATA

(71) Applicant: Abiomed, Inc., Danvers, MA (US)

(72) Inventor: Leah Gaffney, Cambridge, MA (US)

(73) Assignee: Abiomed, Inc., Danvers, MA (US)

( * ) Notice: Subject to any disclaimer, the term of this patent is extended or adjusted under 35 U.S.C. 154(b) by 0 days.

(21) Appl. No.: 18/971,623

(22) Filed: Dec. 6, 2024

(65) Prior Publication Data

US 2025/0191762 A1 Jun. 12, 2025

Related U.S. Application Data

(60) Provisional application No. 63/639,965, filed on Apr. 29, 2024, provisional application No. 63/607,855, filed on Dec. 8, 2023.

(51) Int. Cl.
*G06F 16/28* (2019.01)
*G16H 10/60* (2018.01)
*G16H 50/20* (2018.01)

(52) U.S. Cl.
CPC .................................. *G16H 50/20* (2018.01)

(58) Field of Classification Search
CPC ........ G16H 50/20; G16H 10/60; G16H 50/70; A61F 2/82; A61F 2/07; A61M 60/13; A61M 60/216; A61M 60/508; A61M 60/592; G06N 3/045; G06N 3/0464; G06N 3/02; G06N 5/00; G06F 40/295
See application file for complete search history.

(56) References Cited

U.S. PATENT DOCUMENTS

2021/0216822 A1* 7/2021 Paik ........................ G10L 15/22
2023/0170064 A1 6/2023 Chen et al.
2023/0252064 A1 8/2023 Ozaki et al.
2023/0394654 A1* 12/2023 Hampe ................ G06T 7/0012

OTHER PUBLICATIONS

International Search Report and Written Opinion of the International Searching Authority mailed Mar. 5, 2025 for International Application No. PCT/US2024/058858.
Kashirina, I., et al., "Search for Clinical Entities Associated with Atherosclerosis Using Methods of Natural Language Processing." 2023 Applied Mathematics, Computational Science and Mechanics: Current Problems (AMCSM). IEEE, 2023. 6 pages.
Pella, Z., et al., "Application for text processing of cardiology medical records." 2018 World Symposium on Digital Intelligence for Systems and Machines (DISA). IEEE, 2018, pp. 169-174.

* cited by examiner

*Primary Examiner* — Maroun P Kanaan
(74) *Attorney, Agent, or Firm* — Pierce Atwood LLP

(57) ABSTRACT

Methods and apparatus for extracting coronary artery disease (CAD) information from unstructured medical text are provided. The method includes receiving unstructured medical text, processing the unstructured medical text using one or more trained natural language processing (NLP) models, wherein the one or more trained NLP models are trained to output CAD information, wherein the CAD information includes predicted coronary lesion information, and displaying an indication of the predicted coronary lesion information on a user interface associated with a computing device.

18 Claims, 9 Drawing Sheets

| | Annotation Guidelines | Context Details |
|---|---|---|
| **VESSEL** | Full vessel names and acronyms<br>{LM, left main, left main artery, left main coronary artery, LMCA}<br>*includes {artery, vessel, branch) as part of vessel name when present | *Include vessels only in the context of describing the vessels as on an image (which may be more than lesion description but may also be describing vessel size, position, calcification, etc).<br>*Exclude vessels mentioned for procedural details (gaining access) |
| *SEVERITY* | Specific information about level of occlusion of a lesion or severity of disease<br>{50%, mild, moderate, severe, patent}<br>*Must be able to be followed by {lesions, stenosis, occlusion, disease, etc.}<br>*Include the full range (60-70%, 60 to 70%) when applicable | *Excludes other severities (severe hypotension, 30-40% ejection fraction) |
| LOCATION | Specific information about locations describing a coronary image<br>{ostial, proximal, distal, mid-third, proximal segment}<br>*"mid to distal" a single entity in "mid to distal LAD"<br>*"mid" and "distal" separate entities in "from the mid to the distal" | *Can include locations of stents or graft anastomoses, not just lesions |
| ***GRAFT*** | Full graft type names and acronyms<br>{LIMA, LIMA graft, IMA, left internal mammary artery, left internal mammary artery graft}<br>*includes {graft} as part of name when present | |
| LESION | Words that indicate the presence of lesion or disease<br>{lesions, stenosis, occlusion, disease}<br>*CTO (chronic total occlusion) is therefore broken into "chronic total" that describes the severity and "occlusion" that indicates the presence of the lesion | |

FIG. 1A

| | | |
|---|---|---|
| **No Verb / Minimal Grammar** | | "**LAD**: **Lesion** Description (**Stenosis** % *40*, *mild*, <10mm, calcified, TIMI flow 3)."<br>"Mid **rca** to dist **rca** lesion, *65-70%* stenosed."<br>"*80%* calcified proximal **LAD**." |
| **Simple Grammatical Sentence** | **Single lesion** | "The **left main artery** is heavily calcified and has a *70%* distal **stenosis**." |
| | **Single severity describing multiple vessels** | "Proximal **cx**, **lad** and **lm** are *patent*." |
| **Compound Sentences**<br>(multiple lesions in a single sentence) | | "*90%* proximal **LCx** with at least one **occluded OM** with faint left to left collaterals."<br>**Left anterior descending artery** seemed to have *70-80%* ostial *severe* **stenosis** followed by *60%* proximal diffuse **stenosis.** |
| **Multi-Sentence**<br>(single lesion info spans >1 sentence) | | "The **left main coronary artery** is of moderate length, large vessel. It bifurcates into the **LAD** and **LCX coronary arteries**. It has a focal, eccentric, and calcified *80%* **stenosis** in its distal third."<br>"The ***left internal mammary artery graft*** anastomosis is at the mid **left anterior descending artery**. There was *100%* **occlusion** in the mid to distal graft." |

FIG. 1C

| | Location Start | Vessel Start | Location End | Vessel End | Graft | Severity |
|---|---|---|---|---|---|---|
| "Mid **rca** to dist **rca** lesion, *65-70%* stenosed." | Mid | RCA | Distal | RCA | | 65-70% |
| "The **left main artery** is heavily calcified and has a *70%* distal **stenosis**." | Distal | LM | | | | 70% |
| **Left anterior descending artery** seemed to have *70-80%* ostial *severe* **stenosis** followed by *60%* proximal diffuse **stenosis** | Ostial | LAD | | | | 70-80% |
| | Proximal | LAD | | | | 60% |
| "The ***left internal mammary artery graft*** anastomosis is at the mid **left anterior descending artery**. There was *100%* **occlusion** in the mid to distal graft." | | LAD | | | LIMA | 100% |
| "The **left main coronary artery** is of moderate length, large vessel. It bifurcates into the **LAD** and **LCX coronary arteries**. It has a focal, eccentric, and calcified *80%* **stenosis** in its distal third." | Distal third | LM | | | | 80% |

FIG. 2A

| Types | Examples | Lesion start | | Lesion End | |
|---|---|---|---|---|---|
| | | L1 | *V1* | L2 | *V2* |
| Just a vessel with no location | The ***left main coronary artery*** lesion has 80% stenosis. | - | *lm* | - | - |
| Single location within single vessel | The ***left main coronary artery*** has a **distal** 80% stenosis. | dist | *lm* | - | - |
| Start and end locations within a single vessel (lesion spans >1 third) | **Mid** to **dist *rca*** lesion, 65-70% stenosed. | mid | - | dist | *rca* |
| | **Mid *rca*** to **dist *rca*** lesion, 65-70% stenosed.<br>*(*rca refers to same vessel, may / may not be written twice)* | mid | *rca* | dist | *rca* |
| Lesion spans multiple vessels | There was a 70% tubular stenosis from the **distal *right coronary artery*** to the **proximal *right posterior atrioventricular artery.*** | dist | *rca* | prox | *rpav* |
| | Angiogram revealed 80% stenosis of the **distal *LM*/ostial *LAD.*** | dist | *lm* | ostial | *lad* |

FIG. 2B

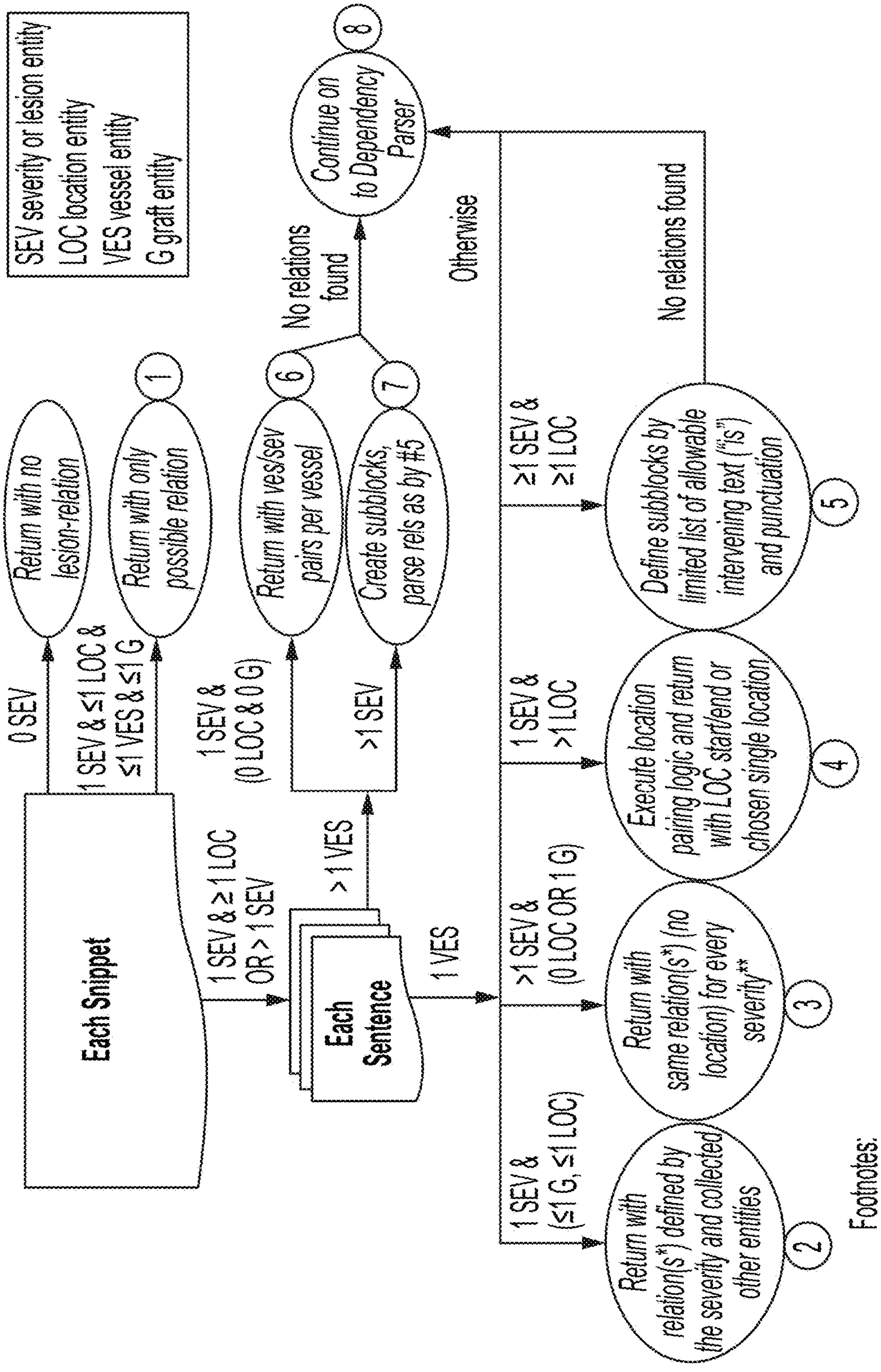

Footnotes:
For all allow single location entity to be splittable to "prox to mid vessel" → prox vessel, mid vessel
*"1st and 2nd diagonals" → one entity that can be split to two relations
**Some severity entities may be refering to the same lesion "mild severity about 20%". In labeling and logic, identify and prefer more specific numeric information to supercede, eliminating redundant qualitative severity info.

FIG. 3

METHODS AND APPARATUS FOR AUTOMATED EXTRACTION OF CORONARY ARTERY DISEASE INFORMATION FROM UNSTRUCTURED MEDICAL DATA

CROSS-REFERENCE TO RELATED APPLICATIONS

This application claims the benefit under 35 U.S.C. § 119(c) to U.S. Provisional Patent Application No. 63/607,855, filed Dec. 8, 2023, and titled, "METHODS AND APPARATUS FOR AUTOMATED EXTRACTION OF CORONARY ARTERY DISEASE INFORMATION FROM UNSTRUCTURED MEDICAL DATA," and claims priority to U.S. Provisional Patent Application No. 63/639,965, filed Apr. 29, 2024, and titled "METHODS AND APPARATUS FOR AUTOMATED EXTRACTION OF CORONARY ARTERY DISEASE INFORMATION FROM UNSTRUCTURED MEDICAL DATA," the entire contents of each of which is incorporated by reference herein.

FIELD OF INVENTION

This disclosure relates to techniques for automated extraction of coronary artery disease information from unstructured medical data.

BACKGROUND

Percutaneous coronary interventions (PCIs) are minimally invasive procedures that are used to open blocked coronary arteries. Examples of PCIs include balloon angioplasties, angioplasties with a stent, and atherectomies. Patients with blocked coronary arteries may be candidates for PCI with some patients qualifying for a regular PCI, other patients qualifying for high risk PCI depending on various risk factors, and yet other patients not qualifying for high risk PCI owing to major risk factors. Some patients who, based on their risk factors, may ordinarily not qualify for a high risk PCI procedure, may be considered for such procedures if mechanical circulatory support (e.g., provided by an implantable blood pump) is provided to the patient during the PCI procedure.

SUMMARY

Described herein are systems and methods for using one or more models to extract coronary artery disease (CAD) information from unstructured medical data (e.g., echocardiographs, angiography reports). The extracted CAD information may be used, at least in part, to identify patients that are at a high risk for complications and may benefit from mechanical circulatory support during PCI procedures.

In some embodiments, a computer-implemented method of extracting coronary artery disease (CAD) information from unstructured medical text is provided. The method includes receiving unstructured medical text, processing the unstructured medical text using one or more trained natural language processing (NLP) models, wherein the one or more trained NLP models are trained to output CAD information, wherein the CAD information includes predicted coronary lesion information, and displaying an indication of the predicted coronary lesion information on a user interface associated with a computing device.

In one aspect, the one or more trained NLP models includes at least one named entity recognition (NER) model and/or at least one relation extraction (REL) model. In another aspect, the at least one NER model includes a machine learning based NER model and a non-machine learning based NER model. In another aspect, the machine learning based NER model comprises a convolutional neural network. In another aspect, the non-machine learning based NER model comprises a rule-based architecture. In another aspect, the method further includes determining, based at least in part, on an output of the machine learning based NER model and an output of the non-machine learning based NER model, a set of entity annotations, wherein the set of entity annotations are provided as input to the at least one REL model. In another aspect, the one or more trained NLP models includes at least one NER model and at least one REL model, an output of the of the at least one NER model is provided as input to the at least one REL model, and the at least one REL model is trained to output the CAD information. In another aspect, the at least one REL model comprises a rule-based architecture. In another aspect, the at least one REL model is trained to identify and relate information about individual CAD lesions from the unstructured medical text. In another aspect, the at least one NER model is trained to identify keywords and/or spans that define one or more CAD lesions from the unstructured medical text.

In another aspect, receiving unstructured medical text comprises receiving unstructured medical text from an electronic health record. In another aspect, the unstructured medical text comprises text from one or more of a medical history document, a physical examination document, a progress notes document, a procedural report, or a diagnostic imaging report. In another aspect, the unstructured medical text comprises text from an echocardiograph or an angiography report. In another aspect, the unstructured medical text comprises text associated with a group of patients.

In another aspect, the method further includes dividing the unstructured medical text into smaller segments, and processing the unstructured medical text using one or more trained NLP models comprises processing the smaller segments. In another aspect, processing the unstructured medical text using one or more NLP models comprises extracting from the unstructured medical text, information for a lesion, the information including vessel information associated with the lesion, location information within the vessel, and severity information associated with the lesion. In another aspect, processing the unstructured medical text using one or more NLP models further comprises extracting from the unstructured medical text, vessel size information associated with the lesion and/or quality information associated with the lesion. In another aspect, processing the unstructured medical text using one or more NLP models comprises using sentence structure information to determine an association between at least a portion of the unstructured medical text and the CAD information. In another aspect, the sentence structure information includes a complexity of a sentence in the unstructured medical text.

In another aspect, the one or more NLP models includes a relation extraction (REL) model, processing the unstructured medical text using one or more NLP models comprises processing the unstructured medical text using the REL model, and the predicted coronary lesion information includes first information associated with a start of a lesion and second information associated with an end of the lesion. In another aspect, each of the first information and the second information includes location information and vessel feature information. In another aspect, the CAD information output from the one or more NLP models includes information about existing stents/grafts, collaterals and/or medical procedures associated with a patient. In another aspect, the information about existing stents/grafts includes one or more of graft type information, anastomosis side, severity information associated with a graft, or location of a lesion with respect to the graft or an anastomosis site. In another aspect, the information about collaterals and/or medical procedures associated with a patient comprises information about a type of medical procedure performed and/or an amount of residual stenosis following a medical procedure. In another aspect, displaying an indication of the predicted coronary lesion information on a user interface associated with a computing device comprises displaying a recommendation of whether to perform a medical procedure based, at least in part, on the predicted coronary lesion information. In another aspect, the medical procedure includes implantation of a heart pump device in a heart of a patient.

In some embodiments, a controller for a mechanical circulatory support device is provided. The controller includes at least one hardware processor configured to receive unstructured medical text, and process the unstructured medical text using one or more trained natural language processing (NLP) models, wherein the one or more trained NLP models are trained to output coronary artery disease (CAD) information, wherein the CAD information includes predicted coronary lesion information. The controller further includes a display configured to display on a user interface, an indication of the predictive coronary lesion information.

In one aspect, the one or more trained NLP models includes at least one named entity recognition (NER) model and/or at least one relation extraction (REL) model. In another aspect, the at least one NER model includes a machine learning based NER model and a non-machine learning based NER model. In another aspect, the machine learning based NER model comprises a convolutional neural network. In another aspect, the non-machine learning based NER model comprises a rule-based architecture. In another aspect, the at least one hardware processor is further configured to determine, based at least in part, on an output of the machine learning based NER model and an output of the non-machine learning based NER model, a set of entity annotations, wherein the set of entity annotations are provided as input to the at least one REL model. In another aspect, the one or more trained NLP models includes at least one NER model and at least one REL model, an output of the of the at least one NER model is provided as input to the at least one REL model, and the at least one REL model is trained to output the CAD information. In another aspect, the at least one REL model comprises a rule-based architecture. In another aspect, the at least one REL model is trained to identify and relate information about individual CAD lesions from the unstructured medical text. In another aspect, the at least one NER model is trained to identify keywords and/or spans that define one or more CAD lesions from the unstructured medical text.

In another aspect, the at least one hardware processor is configured to receive the unstructured medical text from an electronic health record. In another aspect, the unstructured medical text comprises text from one or more of a medical history document, a physical examination document, a progress notes document, a procedural report, or a diagnostic imaging report. In another aspect, the unstructured medical text comprises text from an echocardiograph or an angiography report. In another aspect, the unstructured medical text comprises text associated with a group of patients. In another aspect, the at least one hardware processor is further configured to divide the unstructured medical text into smaller segments, and process the unstructured medical text using one or more trained NLP models by processing the smaller segments.

In another aspect, the at least one hardware processor is configured to process the unstructured medical text using one or more NLP models by extracting from the unstructured medical text, information for a lesion, the information including vessel information associated with the lesion, location information within the vessel, and severity information associated with the lesion. In another aspect, the at least one hardware processor is configured to process the unstructured medical text using one or more NLP models by extracting from the unstructured medical text, vessel size information associated with the lesion and/or quality information associated with the lesion. In another aspect, the at least one hardware processor is configured to process the unstructured medical text using one or more NLP models by using sentence structure information to determine an association between at least a portion of the unstructured medical text and the CAD information. In another aspect, the sentence structure information includes a complexity of a sentence in the unstructured medical text.

In another aspect, the one or more NLP models includes a relation extraction (REL) model, the at least one hardware processor is configured to process the unstructured medical text using one or more NLP models by processing the unstructured medical text using the REL model, and the predicted coronary lesion information includes first information associated with a start of a lesion and second information associated with an end of the lesion. In another aspect, each of the first information and the second information includes location information and vessel feature information. In another aspect, the CAD information output from the one or more NLP models includes information about existing stents/grafts, collaterals and/or medical procedures associated with a patient. In another aspect, the information about existing stents/grafts includes one or more of graft type information, anastomosis side, severity information associated with a graft, or location of a lesion with respect to the graft or an anastomosis site. In another aspect, the information about collaterals and/or medical procedures associated with a patient comprises information about a type of medical procedure performed and/or an amount of residual stenosis following a medical procedure. In another aspect, the at least one hardware processor is configured to display an indication of the predicted coronary lesion information on a user interface associated with a computing device by displaying a recommendation of whether to perform a medical procedure based, at least in part, on the predicted coronary lesion information. In another aspect, the medical procedure includes implantation of a heart pump device in a heart of a patient.

BRIEF DESCRIPTION OF DRAWINGS

FIG. 1A illustrates components of an example data model that may be used to characterize coronary artery disease (CAD) information, in accordance with some embodiments of the present technology.

FIG. 1C illustrates further examples of extracting CAD information from unstructured medical data using sentence structure information, in accordance with some embodiments of the present technology.

FIG. 2A illustrates application of an example relation extraction (REL) model to determine CAD information, in accordance with some embodiments of the present technology.

FIG. 2B illustrates examples of extracting lesion location features from text in a medical document, in accordance with some embodiments of the present technology.

FIG. 3 is block diagram of a logic flow for an REL module configured to relate tokens in analyzed text, in accordance with some embodiments of the present technology.

DETAILED DESCRIPTION

Figure 1B:
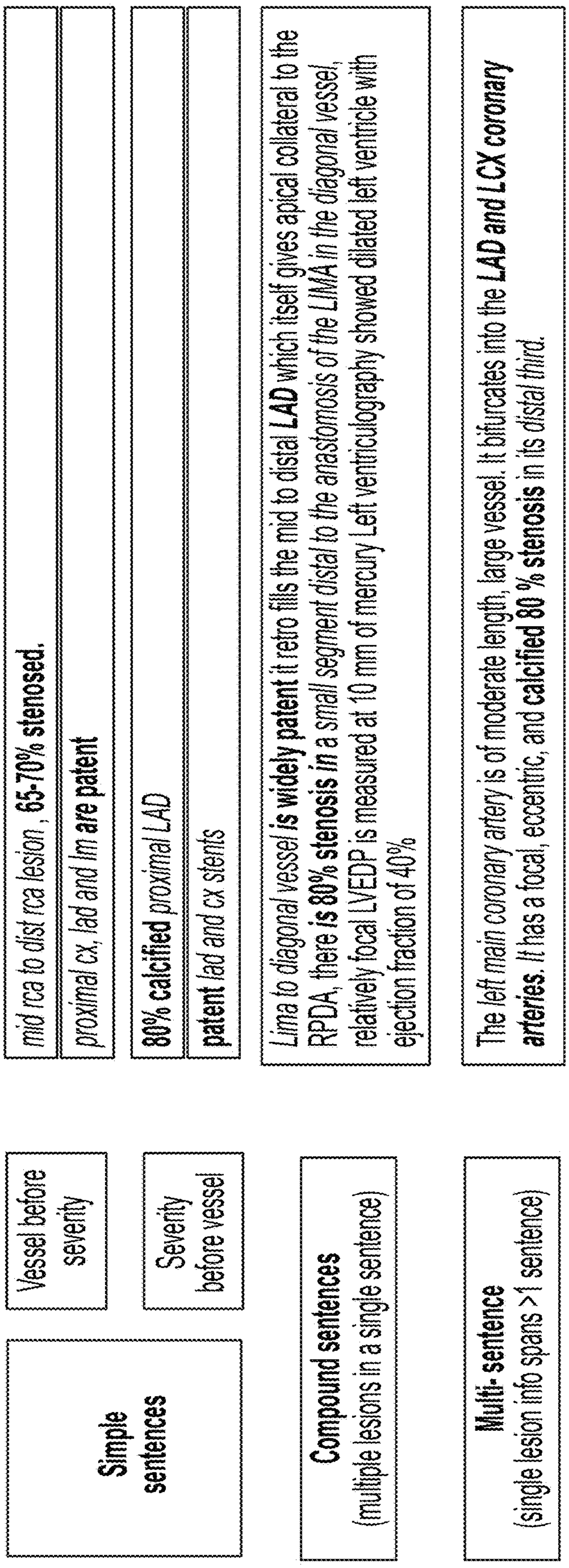
FIG. 1B illustrates examples of extracting CAD information from unstructured medical data using sentence structure information, in accordance with some embodiments of the present technology.

As is known, Percutaneous Coronary Interventions (PCIs) may be used to open a patient's blocked coronary artery, such as a patient suffering from coronary artery disease. Unfortunately, using conventional risk factor analyses, a significant portion of patients who would benefit from PCI are not qualified even for a high-risk PCI owing to major risk factors. Some of those patients may qualify for a PCI if, during the procedure, the patient receives mechanical circulatory support (e.g., via a percutaneous mechanical heart pump) to temporarily support the heart during the procedure and ensure that blood flow is being maintained to critical organs. Such a procedure may be referred to as "Protected PCI®" in that the heart pump serves to protect the patient's heart during the PCI procedure.

Information in a patient's electronic health record (EHR) may be used to assess whether a patient may be a candidate for Protected PCI®. However, such information may be stored in ways that make it challenging to automatically extract relevant features to determine a patient's eligibility. For instance, although some features of eligibility (e.g., co-morbidities, coronary artery disease (CAD) diagnosis using billing codes) may be relatively straightforward to extract from structured data in an EHR, other features may be represented in unstructured text (e.g., echocardiographs, angiography reports, etc.) that is harder to parse with automatic extraction tools. To this end, some embodiments are directed to data-driven techniques to extract CAD information (e.g., CAD lesion details) from unstructured medical data, which may then be used, for example, as one or more features to determine whether a patient may be a suitable candidate for Protected PCI®. Improved automatic extraction techniques for CAD information from a patient's unstructured medical data may result in improved prediction for whether the patient will benefit from use of a mechanical heart pump during a PCI procedure.

In some embodiments, text data relevant to CAD may be extracted from a collection of clinical reports that includes unstructured text data. The extracted text data may be used to train, validate, and/or test one or more natural language processing (NLP) models for automatically extracting text from unstructured medical data. For example, the one or more NLP models may include one or more non-machine learning (non-ML) NLP models (e.g., rule-based regular expression matching models, etc.) and/or one or more machine learning based (ML-based) NLP models (e.g., neural network models, transformer models, etc.). In some embodiments, the one or more NLP models may include a named entity recognition (NER) model, which may be used to identify keywords and spans that may define one or more CAD lesions. In some embodiments, a relation extraction (REL) model may be used to collect and relate the information about individual CAD lesions. In some embodiments, the output of a first NLP model (e.g., an NER model) may be provided as input to a second NLP model (e.g., an REL model) configured to provide extracted CAD information (e.g., values for features that may be used, at least in part, to predict candidacy for a Protected PCI®. In this way, words or word phrases in the text may be identified using an NER model and an REL model may be used to identify how the words or word phrases identified by the NER model relate or group to define lesions.

In some embodiments, training data used to train one or more NLP models for extracting CAD information from unstructured medical information may be curated from data included in a data registry. For instance, the data registry may include de-identified patient data (e.g., diagnostic coronary angiogram reports, catheterization lab reports) entered via an electronic data capture (EDC) system for patients in which a temporary heart pump was implanted. The curated data may simulate EHR data in text form, which may be useful for training and/or evaluating one or more NLP models, examples of which are described herein. In some embodiments, the curated text data may be chopped up into smaller (e.g., paragraph-like) segments, referred to herein has "snippets." The snippets may represent smaller processable components that include lesion description information, which can be labeled and provided as input to NLP models (e.g., NER and REL models) for training the models.

In some embodiments, information about CAD lesions in a patient's EHR may include at least three types of information used to characterize a lesion-vessel information (e.g., gross location of the lesion), location within the vessel (e.g., finer location of the lesion), and severity information (e.g., total occlusion, percent occlusion value, percent occlusion range, descriptive category information (e.g., patent, open, mild, moderate, severe occlusion)). Additionally, some embodiments include additional information used to characterize a vessel including, but not limited to, vessel size (e.g. normal, medium, large) and lesion qualities (e.g., diffuse, discrete, calcified, length, etc.), etc. In some embodiments, severity information may be represented in the unstructured medical data in different ways. For instance, severity may be indicated using quantitative text (e.g., 90%, less than 90%, >90%, etc.) and/or a qualitative description (e.g., open, patent, normal clear, severe, occluded, chronically totally occluded (CTO), etc.). In some embodiments, one or more NLP models may be used to extract such types of information from unstructured medical data for a patient or group of patients.

In some embodiments, information associated with central and/or peripheral CAD lesions may be extracted. For instance, central lesions may include lesions in the vessels of the heart itself, whereas peripheral lesions may include lesions in peripheral vessels such as the right/left iliac vessels (e.g., common iliac, external iliac, internal iliac).

In some embodiments, a large collection of clinical documents may be analyzed to extract text, which may be used to generate (e.g., by training) one or more NLP models. For instance, the collection of clinical documents may include documents associated with patients' medical history and physical examination, progress notes, procedural reports, diagnostic imaging reports, etc. In some embodiments, clinical documents that include diagnostic information in addition to, or rather than, merely procedure information, may be used to extract text, which may be used to train an NLP model. For instance, clinical documents with sections having headings "findings" or "angiographic findings" may be more likely to include relevant text for further analysis and/or extraction. Some non-limiting examples of such sections of text are provided below:

Coronary arteries: The coronary circulation is right dominant. The left main has a normal origin and bifurcates normally into the LAD and circumflex. The left anterior descending arises normally from the left main. The left circumflex arises normally from the left main and gives rise to 2 obtuse marginals.

Left main: Large. Mild diffuse disease.

LAD: Medium-sized. Proximal vessel lesion: There is a 100%.

Left Circumflex: Medium-large. Moderate diffuse disease. Proximal vessel lesion. There is an 80% stenosis.

1st obtuse marginal: Large. Moderate disease. Ostial lesion: There is an 85% stenosis.

Right coronary: Medium-sized. Proximal vessel lesion: There is a 100%.

In some embodiments, CAD information extracted from unstructured medical data, in accordance with the techniques described herein, may include information about existing stents/grafts, collaterals, and/or procedures. For example, CAD information for existing grafts may include information describing the graft type (e.g., saphenous vein graft (SVG), left internal mammary artery (LIMA), etc.), anastomosis side (e.g., mid LAD, etc.), severity information (e.g., total occlusion, percent occlusion value, percent occlusion range, descriptive category information (e.g., mild, moderate, severe occlusion)), and location of lesion with respect to graft (e.g., mid-graft) or anastomosis site (e.g., just distal to anastomosis). CAD information for collaterals or procedures may include information about the type of procedure performed (e.g., angioplasty) and/or an amount of residual stenosis (e.g., 20% residual stenosis).

FIG. 1A shows an example of a named entity recognition (NER) data model in which entity definitions and annotation guidelines may be used to map text to CAD information, in accordance with some embodiments. As shown in FIG. 1A, vessel name, lesion severity, and lesion location may be considered as primary entities, with graft and lesion features included as secondary entities. In some cases, the text may include incomplete information about one or more of the primary entities and the missing primary entity information may be inferred based on downstream assumptions. It should be appreciated that modifications to the data model shown in FIG. 1A may be made. For instance, in one implementation, the lesion entity may be fully absorbed into the severity entity. The current approach may attempt to mimic the grammatical structures of the sentences where some sentences use abbreviated grammar and there may not always be a true severity.

In some embodiments, sentence structure information may be used to extract relevant CAD information. FIG. 1B illustrates non-limiting examples of sentence structure information that may be used to extract CAD information, in accordance with some embodiments of the present disclosure. As shown in FIG. 1B, sentence structure information (e.g., whether the section being analyzed is a simple sentence, a compound sentence, or a multi-sentence) may be used to determine how to associate certain text with CAD information (e.g., vessel identification, location in vessel, severity, etc.) for extraction. FIG. 1C illustrates further non-limiting examples of sentence structure information that may be used to extract CAD information, in accordance with some embodiments of the present disclosure. As shown in FIG. 1C, different levels of sentence structure complexity (e.g., including a no verb/minimal grammar level of complexity) may be used to determine how to associate certain text with CAD information.

In some embodiments, unstructured text within a clinical document may be analyzed to map text to various features included in the extracted CAD information. In some embodiments, a relational extraction (REL) data model may be used to organize the data to define each individual lesion. The REL data model may recognize the need to separate the start and end of the lesion, which are sometimes defined separately in the text and/or the lesion may span two vessels. In some embodiments, vessel start and severity may be required for each lesion (or severity may be replaced by a "lesion" entity). Sentences that describe multiple lesions may produce two distinct lesion-relations. If there are multiple, redundant severities describing the same lesion (as in 70-80% ostial severe stenosis), the data model may describe only a single lesion and may prefer the numerical, more precise information (e.g., "70-80%" versus "severe"). FIG. 2A illustrates an example REL data model that may be used to organize extracted data to define individual lesions, in accordance with some embodiments of the present disclosure.

FIG. 2B illustrates an example of extracting CAD information values for lesion location, in accordance with some embodiments. In the example of FIG. 2B, example sentences from a medical document are analyzed to extract relevant CAD information for a lesion including location (L1) and vessel (V1) features for the lesion start and location (L2) and vessel (V2) features for the end of the lesion. In some instances, values for each of the features L1, V1, L2, and V2 may be extracted from the example sentences. In other instances, only a subset of the values for the features may be extracted. In some embodiments in which only a subset of the values are extracted, values for the missing features may be inferred from other data in the medical document or elsewhere in the patient's electronic health record. Although the example shown in FIG. 2B includes values for four features to describe lesion location, it should be appreciated that other schema including fewer than or more than four features may alternatively be used. For instance, in some embodiments, location (L) and vessel (V) may be collapsed into a single feature.

In some embodiments, a rules-based REL module may be defined. The rules-based REL module may start with simple co-occurrence rules and may progress to more advanced grammatical token dependency rules (e.g., "pair the object and subject of the same verb if the subject is a "vessel" entity and the subject is a "lesion" entity"). FIG. 3 illustrates an example REL module logic flow that may be used in accordance with some embodiments of the present disclosure. If none of the co-occurrence rules are met, the sentence may be complex enough to need grammatical analysis and adjudication of which words belong together which can possibly be achieved by a dependency parser (e.g., based on part of speech predictions for each token in the text and likely syntactic relations (or "dependencies") between the tokens in each sentence).

Figure 4A:
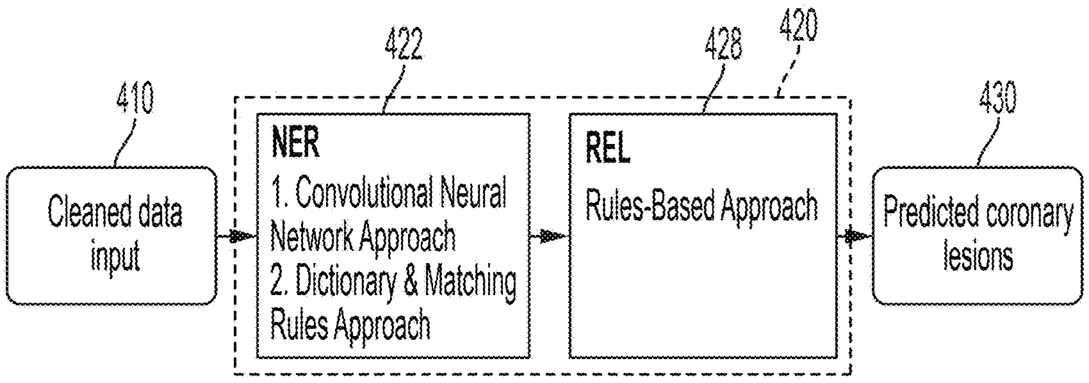
FIG. 4A is a flowchart of a process for determining CAD information using one or more natural language processing (NLP) models, in accordance with some embodiments of the present technology.

FIG. 4A illustrates a process for determining CAD information from medical information using one or more natural language processing (NLP) models 420 in accordance with some embodiments. As shown in FIG. 4A, cleaned data 410 (e.g., curated data from a data registry, processed data from an electronic health record, etc.) may be provided as input to one or more named entity recognition (NER) models 422. As described herein, cleaned data 410 may include unstructured medical text that has been divided into smaller segments (e.g., paragraphs, sentences, individual data entries, portions of sentences, etc.) for processing by NLP model(s) 420. In the example shown in FIG. 4A, the cleaned data is provided as input to a machine learning based model (e.g., a convolutional neural network) and a non-machine learning based model (e.g., a dictionary and matching rules model). It should be appreciated, however, that in some embodiments only a machine learning based model or a non-machine learning based model may be used. The output of the named entity recognition model(s) 422 may be provided as input to one or more relation extraction (REL) models 428. The output of the REL model(s) may be information (e.g., predictions) of CAD information 430 (e.g., coronary lesion information) extracted from the cleaned data. For instance, the CAD information 430 may include predicted coronary lesion information for a patient or group of patients.

Figure 4B:
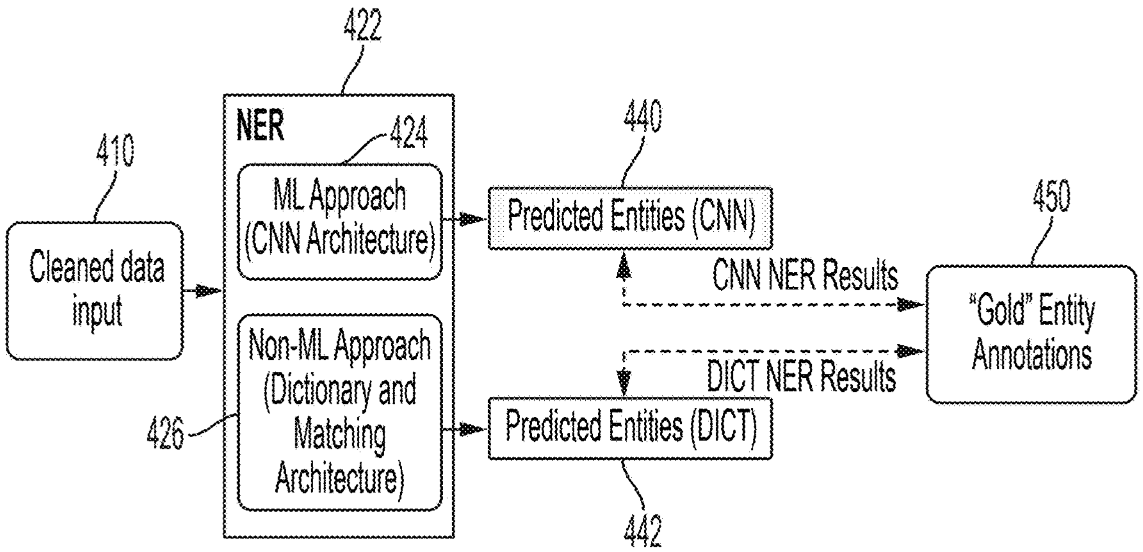
FIG. 4B is a flowchart of a process for determining words and/or word phrases using one or more named entity recognition (NER) models, in accordance with some embodiments of the present technology.

FIG. 4B provides further details on the use of one or more NER models 422 to extract words and/or word phrases from cleaned data 410, in accordance with some embodiments. As shown in FIG. 4B, the output 440 of a first NER model 424 (e.g., an ML-based model) may be compared with the output 442 of a second NER model 426 (e.g. a non-ML-based model) and a set of "Gold" entity annotations 450 may be generated based on the output of both NEL models. For instance, when both of the NEL models 422 extract the same words and/or word phrases, they may be included in the "Gold" entity annotation set 450.

Figure 4C:
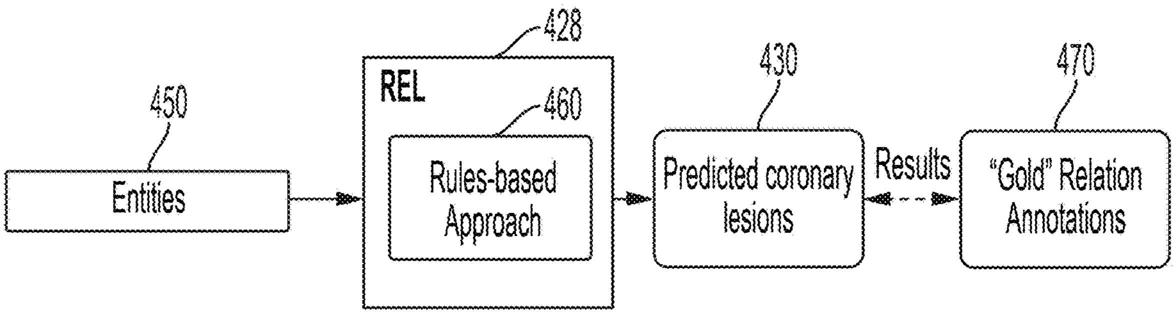
FIG. 4C is a flowchart of a process for relating words and/or word phrases using one or more relation extraction (REL) models, in accordance with some embodiments of the present technology.

FIG. 4C provides further details on the use of one or more REL models 428 to relate words and/or word phrases (collectively "entities" 450) extracted from the cleaned data 410, in accordance with some embodiments. As shown in FIG. 4C, the REL model(s) 428 may include a rules-based architecture 460 and the determined CAD information 430 (e.g., predicted coronary lesion information) output of an REL model (e.g., a rules-based model) may be used to determine a set of "Gold" relation annotations 470.

Figure 5:
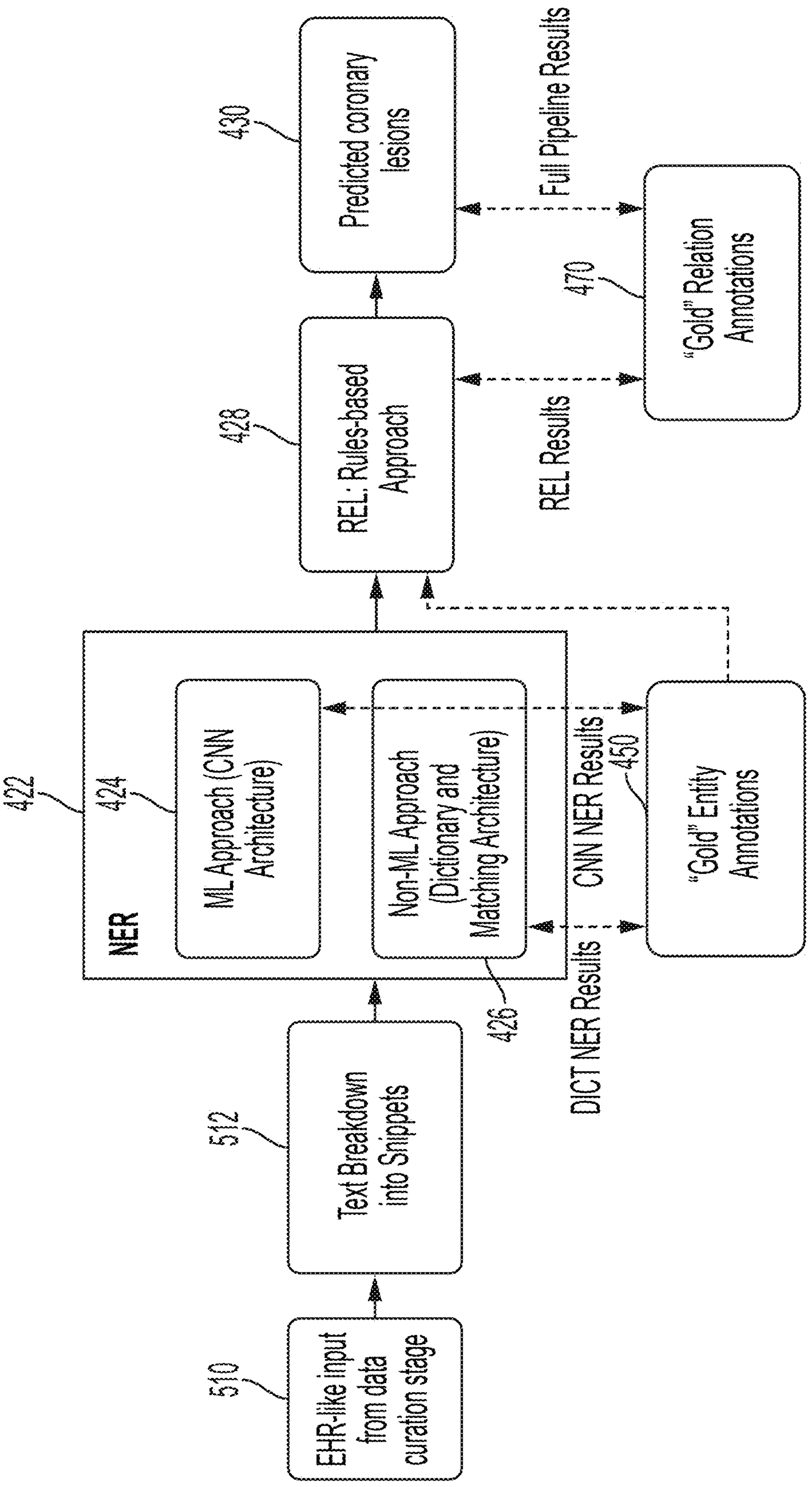
FIG. 5 is a flowchart of an algorithm to extract CAD information from electronic health record text, in accordance with some embodiments of the present technology.

FIG. 5 schematically illustrates a process for extracting CAD information 430 from input text 510 (e.g., EHR data or EHR-like text input that has been curated, for example, from a data registry) in accordance with some embodiments of the present disclosure. As shown, input text 510 may be broken down into smaller segments ("snippets") 512, which may then be provided as input to one or more NER models 422 and one or more REL models 428, examples of which are described herein, with the output being predicted CAD information 430. It should be appreciated that some embodiments may not include all of the NER and REL models shown in FIG. 5. For instance, similar to FIGS. 4A and 4B, FIG. 5 shows two NER models-a first NER model 424 using an ML-based approach (e.g., a CNN-based model) and a second NER model 426 using a non-ML based approach (e.g., a dictionary and matching model). In some embodiments, only a single NER model (e.g., only an ML-based model) may be used. Additionally, FIG. 5 illustrates components for evaluating a comparison between different models (e.g., "Gold" entity annotations 450, "Gold" relation annotations" 470) included in the algorithm pipeline. It should be appreciated that some embodiments may not include such components.

Figure 6:
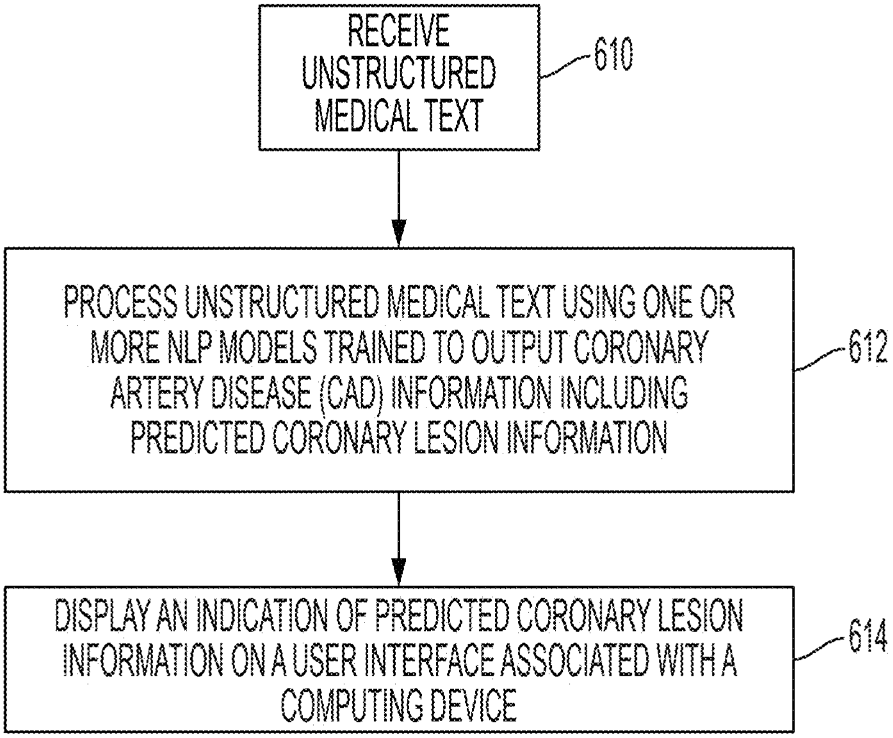
FIG. 6 is a flowchart of a process for processing unstructured medical text to determine coronary lesion information, in accordance with some embodiments of the present technology.

FIG. 6 illustrates a flowchart of a process for determining coronary artery disease (CAD) information from unstructured medical text data, in accordance with some embodiments of the present disclosure. The process may begin in act 610 where unstructured medical text is received. For instance, as described herein the unstructured medical text may be received from an electronic health record associated with a patient or group of patients. The process may then proceed to act 612, where the unstructured medical text is processed using one or more natural language processing (NLP) models trained to output CAD information including predicted coronary lesion information for the patient(s) associated with the unstructured medical text. For instance, the trained NLP models may include one or more NER models and/or one or more REL models, examples of which are described herein. The process may then proceed to act 614, where an indication of the predicted coronary lesion information may be displayed on a user interface associated with a computing device. For instance, one or more values and/or graphs based on the predicted coronary lesion information may be displayed on a display of a controller for a medical device, such as a mechanical circulatory support device. Additionally or alternatively, a recommendation for treating a patient associated with the unstructured medical text may be determined based on the predicted coronary lesion information and an indication of such a recommendation may be displayed on the user interface. In some embodiments, information associated with the predicted coronary lesion information may be transmitted (using one or more wired or wireless networks) to a computing device configured to display the user interface on which the indication of the predicated coronary lesion information may be displayed.

Having thus described several aspects and embodiments of the technology set forth in the disclosure, it is to be appreciated that various alterations, modifications, and improvements will readily occur to those skilled in the art. Such alterations, modifications, and improvements are intended to be within the spirit and scope of the technology described herein. For example, those of ordinary skill in the art will readily envision a variety of other means and/or structures for performing the function and/or obtaining the results and/or one or more of the advantages described herein, and each of such variations and/or modifications is deemed to be within the scope of the embodiments described herein. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, inventive embodiments may be practiced otherwise than as specifically described. In addition, any combination of two or more features, systems, articles, materials, kits, and/or methods described herein, if such features, systems, articles, materials, kits, and/or methods are not mutually inconsistent, is included within the scope of the present disclosure.

The above-described embodiments can be implemented in any of numerous ways. One or more aspects and embodiments of the present disclosure involving the performance of processes or methods may utilize program instructions executable by a device (e.g., a computer, a processor, or other device) to perform, or control performance of, the processes or methods. In this respect, various inventive concepts may be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other tangible computer storage medium) encoded with one or more programs that, when executed on one or more computers or other processors, perform methods that implement one or more of the various embodiments described above. The computer readable medium or media can be transportable, such that the program or programs stored thereon can be loaded onto one or more different computers or other processors to implement various ones of the aspects described above. In some embodiments, computer readable media may be non-transitory media.

The above-described embodiments of the present technology can be implemented in any of numerous ways. For example, the embodiments may be implemented using hardware, software or a combination thereof. When implemented in software, the software code can be executed on any suitable processor or collection of processors, whether provided in a single computer or distributed among multiple computers. It should be appreciated that any component or collection of components that perform the functions described above can be generically considered as a controller that controls the above-described function. A controller can be implemented in numerous ways, such as with dedicated hardware, or with general purpose hardware (e.g., one or more processor) that is programmed using microcode or software to perform the functions recited above, and may be implemented in a combination of ways when the controller corresponds to multiple components of a system.

Further, it should be appreciated that a computer may be embodied in any of a number of forms, such as a rack-mounted computer, a desktop computer, a laptop computer, or a tablet computer, as non-limiting examples. Additionally, a computer may be embedded in a device not generally regarded as a computer but with suitable processing capabilities, including a Personal Digital Assistant (PDA), a smartphone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible formats.

Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks, wired networks or fiber optic networks.

Also, as described, some aspects may be embodied as one or more methods. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

The invention claimed is:

1. A computer-implemented method of extracting coronary lesion information from unstructured medical text, the method comprising:

receiving unstructured medical text from one or more electronic health records;

processing at least some of the unstructured medical text using at least one named entity recognition (NER) model trained to generate first text data, the first text data including keywords and/or spans from the unstructured medical text that define one or more coronary lesions;

processing the first text data using at least one relation extraction (REL) model trained to determine relations between information in the first text data for individual coronary lesions, wherein an output of the at least one REL model includes predicted coronary lesion information for each of the individual coronary lesions; and displaying an indication of the predicted coronary lesion information on a user interface associated with a computing device, wherein processing at least some of the unstructured medical text using at least one NER model comprises:

processing at least some of the unstructured medical text using a machine learning based NER model to generate ML-based text data; and processing at least some of the unstructured medical text using a non-machine learning based NER model to generate non-ML-based text data, and wherein processing the first text data using at least one REL model comprises processing the first text data represented in both the ML-based text data and the non-ML-based text data.

2. The method of claim 1, wherein the first text data represented in both the ML-based text data and the non-ML-based text data includes a set of entity annotations, and wherein the set of entity annotations are provided as input to the at least one REL model.

3. The method of claim 1, wherein the unstructured medical text comprises text from one or more of a medical history document, a physical examination document, a progress notes document, a procedural report, or a diagnostic imaging report.

4. The method of claim 1, further comprising:

dividing the unstructured medical text into smaller segments, wherein processing at least some of the unstructured medical text using at least one NER model comprises providing the smaller segments as input to the at least one NER model.

5. The method of claim 1, wherein the predicted coronary lesion information for each of the individual coronary lesions output from the at least one REL model includes, for each of the individual coronary lesions, vessel information associated with the coronary lesion, location information within the vessel, and severity information associated with the coronary lesion.

6. The method of claim 5, wherein the predicted coronary lesion information for each of the individual coronary lesions output from the at least one REL model further includes vessel size information associated with the coronary lesion and/or quality information associated with the coronary lesion.

7. The method of claim 1, wherein the at least one NER model is trained to use sentence structure information to determine an association between at least a portion of the unstructured medical text and the one or more coronary lesions.

8. The method of claim 7, wherein the sentence structure information includes a complexity of a sentence in the unstructured medical text.

9. The method of claim 1, wherein the predicted coronary lesion information for each of the individual coronary lesions output from the at least one REL model further includes first information associated with a start of the coronary lesion and second information associated with an end of the coronary lesion.

10. The method of claim 1, wherein the predicted coronary lesion information output from the at least one REL model further includes information about a location of a coronary lesion with respect to an existing stent/graft or an anastomosis site.

11. The method of claim 1, wherein displaying an indication of the predicted coronary lesion information on a user interface associated with a computing device comprises displaying a recommendation of whether to perform a medical procedure based, at least in part, on the predicted coronary lesion information.

12. A controller for a mechanical circulatory support device, the controller comprising:

at least one hardware processor configured to:

receive unstructured medical text from one or more electronic health records;

process at least some of the unstructured medical text as input to using at least one named entity recognition (NER) model trained to generate first text data, the first text data including keywords and/or spans from the unstructured medical text that define one or more coronary lesions;

process the first text data using at least one relation extraction (REL) model trained to determine relations between information in the first text data for individual coronary lesions, wherein an output of the at least one REL model includes predicted coronary lesion information for each of the individual coronary lesions, wherein processing at least some of the unstructured medical text using at least one NER model comprises:

processing at least some of the unstructured medical text using a machine learning based NER model to generate ML-based text data; and processing at least some of the unstructured medical text using a non-machine learning based NER model to generate non-ML-based text data, and wherein processing the first text data using at least one REL model comprises processing the first text data represented in both the ML-based text data and the non-ML-based text data; and a display configured to display on a user interface, an indication of the predictive coronary lesion information.

13. The controller of claim 12, wherein the unstructured medical text comprises text from one or more of a medical history document, a physical examination document, a progress notes document, a procedural report, or a diagnostic imaging report.

14. The controller of claim 12, wherein the at least one hardware processor is further configured to:

divide the unstructured medical text into smaller segments, wherein processing at least some of the unstructured medical text as input to at least one NER model comprises providing the smaller segments as input to the at least one NER model.

15. The controller of claim 12, wherein the predicted coronary lesion information for each of the individual coronary lesions output from the at least one REL model includes, for each of the individual coronary lesions, vessel information associated with the coronary lesion, location information within the vessel, and severity information associated with the coronary lesion.

16. The controller of claim 12, wherein the at least one NER model is trained to use sentence structure information to determine an association between at least a portion of the unstructured medical text and the one or more coronary lesions.

17. The controller of claim 12, wherein the predicted coronary lesion information for each of the individual coronary lesions output from the at least one REL model further includes first information associated with a start of the coronary lesion and second information associated with an end of the coronary lesion.

18. The controller of claim 12, wherein the predicted coronary lesion information output from the at least one REL model further includes information about a location of a coronary lesion with respect to an existing stent/graft or an anastomosis site.

* * * * *